United States Patent [19]

Marsh et al.

[11] Patent Number: 4,541,278
[45] Date of Patent: Sep. 17, 1985

[54] PIPELINE CORROSION SENSING DEVICE AND METHOD

[75] Inventors: Glenn A. Marsh; Robert F. Buhl, both of Fullerton, Calif.

[73] Assignee: Union Oil Company of California, Los Angeles, Calif.

[21] Appl. No.: 602,970

[22] Filed: Apr. 23, 1984

[51] Int. Cl.$^4$ .................. G01N 29/04; G01B 5/28
[52] U.S. Cl. ............................. 73/592; 73/86; 73/105; 422/53
[58] Field of Search ............... 73/592, 86, 105, 432 G; 422/53

[56] References Cited

U.S. PATENT DOCUMENTS

| | | | |
|---|---|---|---|
| 2,027,169 | 1/1936 | Harrison | 73/105 |
| 2,397,923 | 4/1946 | Coss | 73/105 |
| 2,460,726 | 2/1949 | Arndt | 73/105 |
| 2,471,009 | 5/1949 | Reason | 73/105 |
| 3,580,062 | 5/1971 | Perthen | 73/105 |
| 3,720,818 | 3/1973 | Spragg et al. | 73/105 |
| 3,973,441 | 8/1976 | Porter | 73/105 |
| 4,295,092 | 10/1981 | Okamura | 73/105 |
| 4,301,677 | 11/1981 | Fisher | 73/86 |
| 4,341,113 | 7/1982 | Gutzwiller, Jr. | 73/105 |

Primary Examiner—Anthony V. Ciarlante
Attorney, Agent, or Firm—Robert J. Baran; Gregory F. Wirzbicki; Dean Sandford

[57] ABSTRACT

The invention provides a sensing device and method to determine irregularities of a pipeline wall arising from corrosion, pitting, gouges, scale and deposits, and dents causing out of round conditions. This sensing device may be carried through a pipeline by a pipeline pig and comprises radial, movable spring-loaded sensing fingers adapted to continuously contact the pipeline inner surface, said sensing fingers preferably being secured to a fluid-tight drum. The sensing fingers are acoustically connected to one or more microphones, which may be confined within the interior chamber of the fluid-tight drum. The microphones, in turn, are electrically connected to a recording device for recording the audio signal the sensing fingers make as they move through the pipeline.

11 Claims, 3 Drawing Figures

U.S. Patent    Sep. 17, 1985    4,541,278
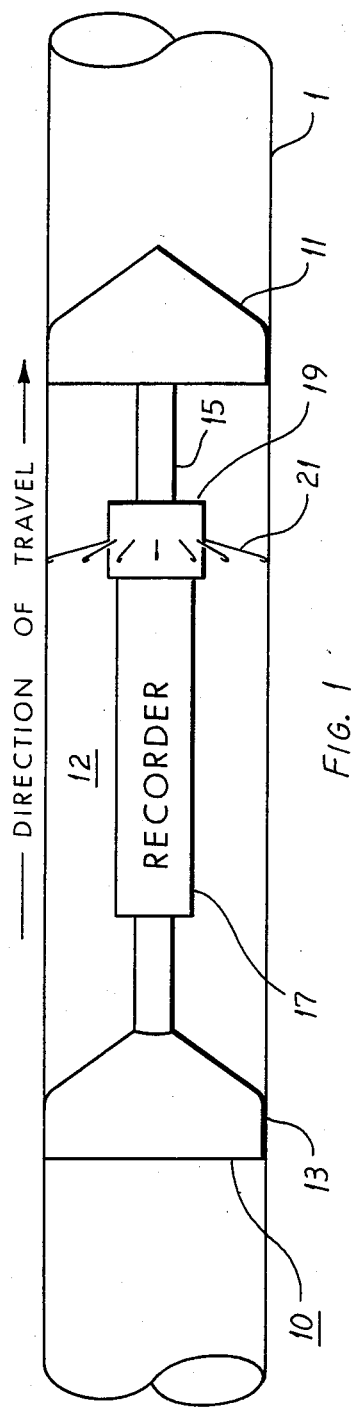
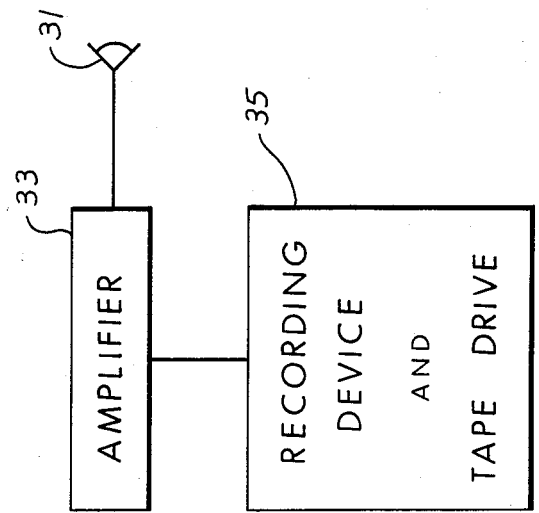
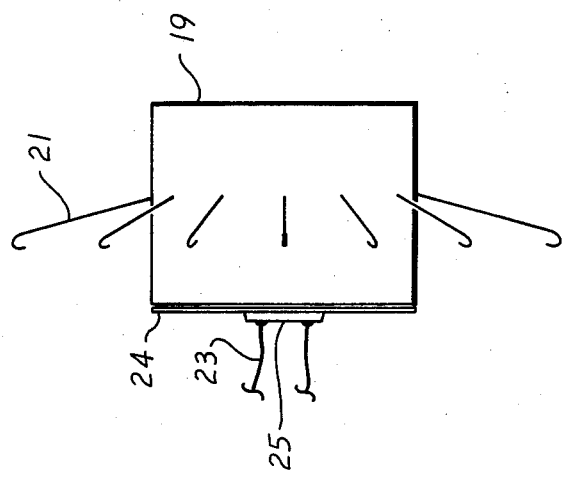

PIPELINE CORROSION SENSING DEVICE AND METHOD

BACKGROUND OF THE INVENTION

1. Field of the Invention

This invention relates to a method and device for determining imperfections in the interior wall of a pipeline. In particular the extent of corrosion of the interior surface of a fluid-carrying pipeline may be appraised by the method and device of this invention.

2. Summary of the Art

The variation in the profile of a surface may be measured by various methods. For example, in U.S. Pat. No. 3,720,818, a stylus, electrically connected to a transducer consisting of two symmetrical coils, is moved along a surface. As the stylus moves normal to the surface changes of inductance in the transducer coils are measured and utilized as a signal of surface roughness. In U.S. Pat. No. 3,580,062 a feeler point is moved along the surface of a work piece to measure roughness. The feeler point is mechanically connected to an electromechanical transducer for converting the relative movement of the feeler point and the work piece into an electrical signal.

Various methods are also known for detecting and profiling the abnormalities of the internal dimensions of various tubular structures, such as pipelines, heat exchanger tubes, etc. which methods include passing a pig adapted to measure changes in the internal walls of a pipeline through the bore. In U.S. Pat. No. 3,973,441 a pipeline pig is disclosed having a wall-contacting shoe which is electrically coupled to an accelerometer and adapted to measure the change in diameter of the pipe as the shoe accelerates or decelerates radially due to contact of the shoe with various corroded internal surfaces and out-of-round portions of the pipeline. U.S. Pat. No. 4,295,092 describes a probe which forms a capacitor with the internal walls of a pipe for measuring the variance in capacitance occurring whenever the probe passes a corroded section of the interior pipewall. In U.S. Pat. No. 4,301,677 an apparatus utilizing cantilever springs coupled to a strain gauge is used to measure changes in the flexing of the cantilevers as the apparatus contacts undulations in the internal surface of a pipe. Similarly, flexure springs are used in the scanner described in U.S. Pat. No. 4,341,113 to measure tube abnormalities through a strain gauge coupled thereto. This scanner also includes an eddy current sensor to locate the tube abnormality in relation to a contiguous external support plate.

All of the above devices require rather sophisticated and sensitive measuring devices to detect internal surface abnormalities; therefore, these devices are not utilized on a frequent, routine basis. It would be desirable to have a device and method that is relatively inexpensive and durable and therefore can be used for frequent monitoring of internal surface corrosion.

Therefore, it is an object of this invention to provide a relatively inexpensive device for frequent use in measuring the internal condition, vis-a-vis corrosion, of the internal surface of a pipeline or other tubular structure.

It is another object of this invention to utilize an acoustic signal to appraise the condition of the interior surface of a fluid-carrying pipeline.

It is another object of this invention to provide a method for recording changes in the condition of the interior surface of a fluid-carrying pipeline with time.

Other objects and advantages of the invention will be apparent from a careful reading of the specification below.

SUMMARY OF THE INVENTION

The present invention provides a sensing device and method to determine flaws or deposits on the interior surface of a pipeline or other tubular object that is not easily inspected during use without dismantling. The sensing device is utilized in combination with a pipeline pig which is adapted to be moved through a pipeline and carry such sensing device. The sensing device has a plurality of radially arranged, spring-loaded sensing fingers that contact the interior wall of a pipeline as the pig moves therethrough. The sensing fingers are acoustically connected to one or more microphones which are, in turn, connected to a recording device. The recording device is preferably located within a fluid-tight housing secured to and carried by the pig. A plurality of sensing fingers are used in order that the entire circumference of the pipeline may be inspected as the pig passes along the pipeline. The vibrations that the individual sensing fingers make as they scrape the interior wall of the pipeline — which vibrations are characteristics of the condition of the interior wall at the point of contact with the sensing finger — are sensed by the microphone(s) and recorded by the recording device, e.g. a tape recorder. The recording device provides a sound recording relating to the condition of the interior pipeline wall. Each of the various wall imperfections found in a pipeline, e.g. corroded surfaces, cracks, pits, gouges, dents, etc., provides its own distinctive audio signal. Thus, the general condition of the interior surface of a pipeline may be monitored on a day to day basis with an increase in the intensity and complexity of the audio signal indicating an increasingly imperfect surface — usually due to corrosion. The point at which any imperfection in the interior of the pipeline occurs may also be determined by comparing the rate of travel of the pig through the pipeline and the time at which said imperfection is recorded by the recording device.

In order to remove dirt and other loose material from the interior walls of the pipeline — to avoid interfering with the above described measurement — it is desirable to first send a scraping pig through the pipeline. Scraping pigs are known in the art and generally include one or more scraping shoes to contact and scrape the interior pipeline wall as the scraping pig moves along the pipeline.

DESCRIPTION OF THE DRAWING FIGURES

FIG. 1 is a schematic illustration of a sensing device of this invention as utilized in determining the condition of the interior walls of a pipe-line.

FIG. 2 is sideview of the instant sensing device showing the arrangement of the radially-located, spring-loaded fingers.

FIG. 3 is a block diagram showing the connection of the microphone and the recording device utilized in the sensing device of this invention.

The figures show a preferred embodiment of the sensing device of the instant invention, wherein like numerals refer to like elements.

DETAILED DESCRIPTION OF THE INVENTION

Referring to FIG. 1, a pipeline pig 10 includes a forward drive cup 11 and a rearward drive cup 13 spaced one from the other by a central bar 15. As shown, the diameter of the drive cups is substantially equivalent to, and preferably slightly larger than, the inner diameter of the pipeline 1 that is to be monitored. The drive cups are of a resilient material, e.g. rubber or plastic, and provide a substantially fluid-tight fit with the interior pipeline walls. Thus the drive cups are pushed by the fluid flowing through the pipeline whereby the pig is propelled through the pipeline by the fluid. The drive cups and the interior walls of the pipeline defines a chamber section 12 which encloses the sensing device of this invention and the appurtenant recording means.

A recorder, which is further described below, is affixed in a fluid-tight housing 17, which is secured to central bar 15 and travels with the sensing device through the pipeline. A drum-shaped housing 19 is also secured to the central bar and is adjacent to said recorder. The drum-shaped housing 19 is coaxial with central bar 15 and has a circumference less than the circumference of the drive cups. The drum-shaped housing is hollow and carries a microphone (not shown) in its interior. A plurality of spring-loaded sensing fingers 21 are arranged radially around the drum-shaped housing and are sized to contact the interior surface of a pipeline to be monitored. The sensing fingers may be fabricated from any material capable of transmitting the vibrations from the point of contact of the sensing fingers and the interior walls of the pipeline to the interior of the drum-shaped housing. For example, the sensing fingers may be of steel, etc. The sensing fingers may be affixed to the drum-shaped housing by such means as welding, bolting, etc.

The sensing device comprising the drum-shaped housing and the radially extending fingers is shown in FIG. 2. FIG. 2 also illustrates the electrical connections 23 from the microphone extending through the back plate 24 of said drum-shaped housing. The drum-shaped housing also has a smaller plate 25 which like the back plate is perforated to enable the electrical connections to pass through.

The hollow interior of the drum-shaped housing provides a chamber for the microphone as well as a suitable acoustic environment to transmit the sound from the spring-loaded fingers to the microphone.

FIG. 3 shows the microphone 31 which transmits the acoustic signal from the interior of the drum-shaped housing through amplifier 33 to the recording device 35. As illustrated, the recording device includes a tape drive to make a permanent record of the audio signal, which can be compared from one pass through the pipeline to another with increasing volume and complexity indicating generally increasing roughness, e.g., corrosion or scale deposition on the interior wall surface.

The instant invention also provides a method for detecting the corrosion of or deposits on the interior walls of a pipeline. This method comprises forming a plurality of sensing fingers to contact said interior walls, moving said fingers along the pipeline to generate an audio signal, passing said audio signal through a microphone to generate an electrical signal, and recording said electrical signal. The changes in the condition of the interior pipeline walls with time can be monitored by carrying out such method at scheduled intervals, e.g., daily, and comparing the volume and complexity of the recorded signal with an earlier (or the initial) run.

The invention is further illustrated by the following example which is illustrative of a specific mode of practicing the invention and is not intended as limiting the scope of the appended claims.

EXAMPLE

In this example, a 1½-mile pipeline, having an inner diameter of 8", is to be surveyed to determine the condition of the interior wall surface. This pipeline carries oil from an offshore oil production platform to shore.

The combination sensing device and pipeline pig of FIG. 1 is prepared for launching at the platform end of the pipeline. The tape recorder is turned on and placed inside the fluid-tight housing of the sensing device. The pig is valved into the pipeline and the oil flow is adjusted to give a fluid velocity through the pipeline of about 2 miles per hour. The pig and the sensing device are received at the shore end in about 45 minutes.

The sensing device is removed from the pipeline at the shore end and the tape is removed from the recorder, rewound, and played back. The tape is found to contain the following sounds which are interpretable in terms of the internal condition of the pipeline.

The initial sound is a steady 'swishing' for about 34 seconds, representing a 100 foot long section of new pipe that runs from the production deck to the ocean floor.

The next 15 minutes of sound is a loud, rattling noise; this represents about a ½ mile of severely corroded pipe.

The sound character gradually becomes quieter, and becomes a fairly steady rumble. This 20 minute segment represents about ⅝ mile of pipeline with only moderate corrosion.

The final portion of the tape is a steady 'swooshing' noise, representing little corrosion, with an occasional short "rushing" noise, which represents deposits of localized corrosion. The final sound is the scraping and banging caused by the entering of the pipeline pig into the receiver at the shore end. The above run is repeated at periodic intervals, e.g., weekly or monthly, and the tapes from each run compared to determine changes in the condition of the interior walls of the pipeline.

While particular embodiments of the invention have been described, it will be understood, of course, that the invention is not limited thereto since many obvious modifications can be made, for example, both the recorder and the microphone may be placed in the interior of the drum-shaped housing. It is intended to include within this invention any such modification as will fall within the scope of the appended claims.

Having now described the invention, we claim:

1. A device to determine conditions in or on the interior walls of a pipeline arising from corrosion, pitting, gouges, scratches, deposits, and dents which comprises a pipeline pig suitably arranged with radial, spring-loaded fingers adapted to contact the interior walls of a pipeline, said sensing fingers being acoustically connected to a microphone and said microphone being electrically connected to a recording device.

2. The device of claim 1 comprising at least 3 spring-loaded fingers axisymmetrically arranged to monitor corrosion over the entire circumference of said interior pipeline wall.

3. The device of claim 2 wherein said pig comprises a central bar secured to and spacing a forward and rearward drive cup each adapted to engage the interior pipeline wall to form a substantially fluid-tight seal.

4. The device according to claim 3 wherein said microphone is confined within a drum-shaped housing, said housing being between said drive cups and coaxial with and secured to said central bar.

5. The device of claim 4 wherein said microphone is electrically connected to a tape recorder secured to said central bar between said drive cups.

6. A device adapted to determine the corrosion on the interior walls of a pipeline which comprises:
(a) a forward drive cup,
(b) a rearward drive cup, each drive cup having a circumference slightly greater than the internal diameter of a pipeline and being resilient to provide a fluid-tight seal within said pipeline,
(c) a central bar securing and spacing said drive cups to provide a chamber section between said drive cups,
(d) a drum-shaped housing, confined within said chamber section, said housing being coaxial with and secured to said central bar, and having a diameter less than the internal diameter of the pipeline,
(e) a plurality of radially extending spring-loaded sensing fingers uniformly spaced about the axis of said drum-shaped housing and adapted to contact the interior walls of the pipeline,
(f) a microphone confined within the interior chamber of said drum-shaped housing in acoustic communication with said sensing fingers, and
(g) recording means positioned within said chamber section and adapted to record an audio signal from said microphone.

7. A sensing device for use with a pipeline pig and adaptable to measure corrosion of or deposits on the interior pipeline walls which comprises a drum-shaped housing, a plurality of radially extending sensing fingers uniformly spaced about the circumference of said housing and adapted to continuously contact the interior pipeline walls, a microphone secured within said housing in acoustic communication with said fingers and means to transmit an audio signal from said microphone to a recorder.

8. A device adapted to determine the corrosion of or deposits on the interior walls of a pipeline which comprises:
(a) sensing means comprising a plurality of fingers adapted to contact the interior surface of the pipeline walls,
(b) a microphone in acoustic communication with said fingers, and
(c) recording means to record an audio signal from said microphone.

9. A method for detecting the corrosion of or deposits on the interior walls of a pipeline which comprises contacting said interior walls with a plurality of sensing fingers, moving said sensing fingers through the pipeline to generate an audio signal, passing said audio signal through a microphone to generate an electrical signal, and recording said electrical signal.

10. A method for determining changes in the condition of the interior walls of a pipeline due to corrosion of or deposits on said interior walls which comprises:
(a) carrying out the method of claim 9 at intervals, and
(b) comparing the recorded electrical signals.

11. The method of claim 10 wherein said intervals are periodic.

* * * * *